United States Patent
Graves et al.

[11] Patent Number: 6,067,475
[45] Date of Patent: May 23, 2000

[54] MICROWAVE ENERGY DELIVERY SYSTEM INCLUDING HIGH PERFORMANCE DUAL DIRECTIONAL COUPLER FOR PRECISELY MEASURING FORWARD AND REVERSE MICROWAVE POWER DURING THERMAL THERAPY

[75] Inventors: Kenneth L. Graves, Golden Valley; Eric N. Rudie, Maple Grove, both of Minn.

[73] Assignee: Urologix, Inc., Minneapolis, Minn.

[21] Appl. No.: 09/186,795

[22] Filed: Nov. 5, 1998

[51] Int. Cl.$^7$ ........................................ A61N 5/02
[52] U.S. Cl. .......................... 607/101; 607/105; 607/113; 607/156
[58] Field of Search ..................................... 607/101, 102, 607/105, 113, 154–156; 606/33

[56] References Cited

U.S. PATENT DOCUMENTS

| | | | |
|---|---|---|---|
| 4,557,272 | 12/1985 | Carr | 607/156 |
| 5,027,829 | 7/1991 | Larsen | 607/101 |
| 5,957,969 | 9/1999 | Warner et al. | 607/156 |

*Primary Examiner*—Lee Cohen
*Attorney, Agent, or Firm*—Kinney & Lange, P.A.

[57] ABSTRACT

A microwave energy delivery system for microwave thermal therapy includes an antenna and a transmission line connected to the antenna. A microwave generating source includes a generator connected to the transmission line and a dual directional coupler for detecting forward power delivered to the antenna and reverse power reflected from the antenna with low uncertainty.

19 Claims, 7 Drawing Sheets

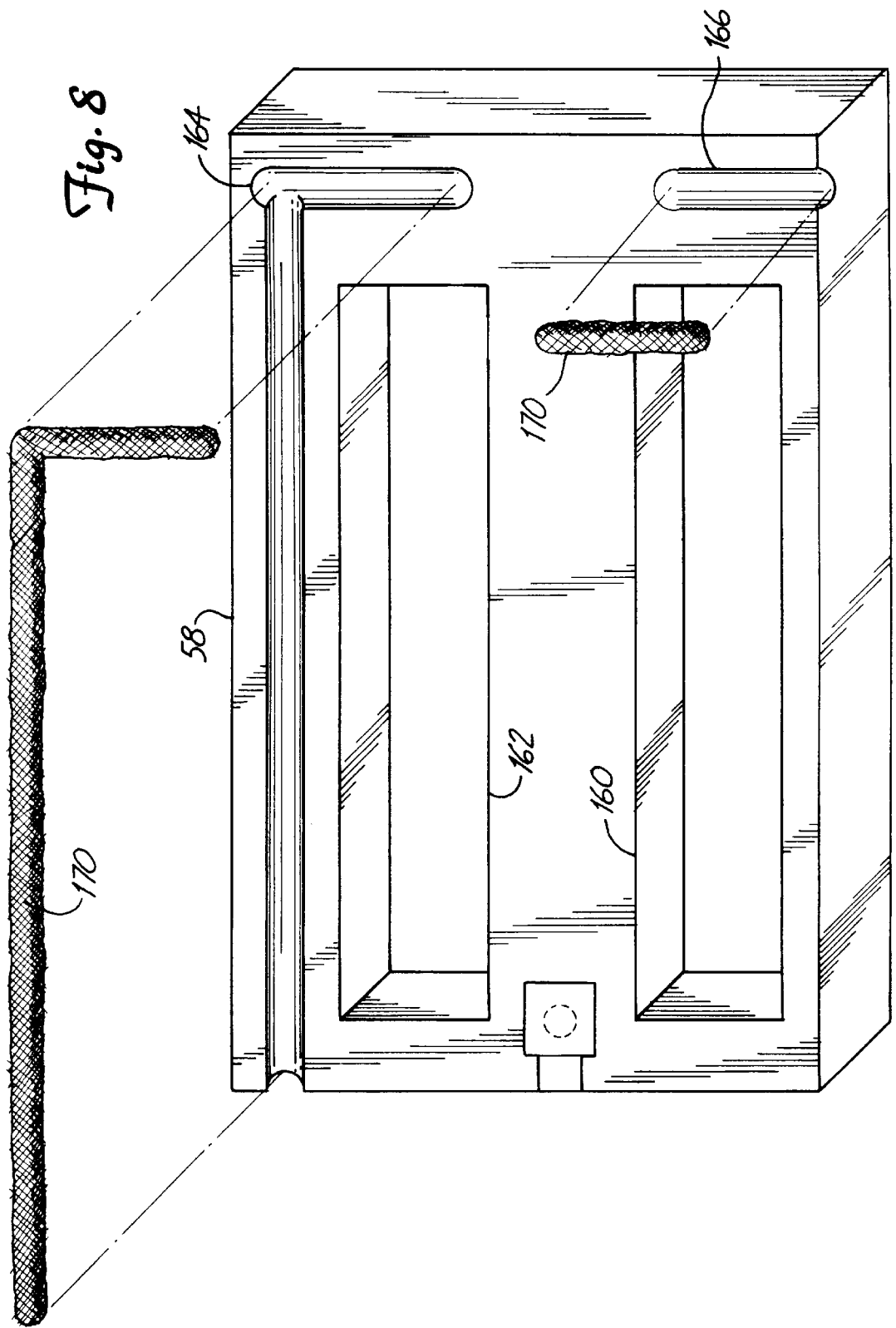

MICROWAVE ENERGY DELIVERY SYSTEM INCLUDING HIGH PERFORMANCE DUAL DIRECTIONAL COUPLER FOR PRECISELY MEASURING FORWARD AND REVERSE MICROWAVE POWER DURING THERMAL THERAPY

CROSS-REFERENCE TO RELATED APPLICATION(S)

Reference is hereby made to U.S. Application Ser. No. 08/621,634 filed Mar. 26, 1996 for VOLTAGE CONTROLLED VARIABLE TUNING ANTENNA by E. Rudie, now U.S. Pat. No. 5,938,692.

BACKGROUND OF THE INVENTION

The present invention relates to the field of microwave thermal therapy of tissue. In particular, the present invention relates to a microwave generating device having a high performance dual directional coupler for precisely measuring forward and reflected power in a microwave antenna transmission line.

The prostate gland is a complex, chestnut-shaped organ which encircles the urethra immediately below the bladder. Nearly one-third of the prostate tissue anterior to the urethra consists of fibromuscular tissue that is anatomically and functionally related to the urethra and bladder. The remaining two-thirds of the prostate is generally posterior to the urethra and is comprised of glandular tissue.

This relatively small organ, which is the most frequently diseased of all internal organs, is the site of a common affliction among older men: BPH (benign prostatic hyperplasia). BPH is a nonmalignant, bilateral nodular expansion of prostate tissue in the transition zone, a periurethral region of the prostate between the fibromuscular tissue and the glandular tissue. The degree of nodular expansion within the transition zone tends to be greatest anterior and lateral to the prostatic urethra, relative to the posterior-most region of the urethra. Left untreated, BPH causes obstruction of the urethra which usually results in increased urinary frequency, urgency, incontinence, nocturia and a slow or interrupted urinary stream. BPH may also result in more severe complications, such as urinary tract infection, acute urinary retention, hydronephrosis and uraemia.

Traditionally, the most frequent treatment for BPH has been surgery (transurethral resection). Surgery, however, is often not an available method of treatment for a variety of reasons. First, due to the advanced age of many patients with BPH, other health problems, such as cardiovascular disease, can warrant against surgical intervention. Second, potential complications associated with transurethral surgery, such as hemorrhage, anesthetic complications, urinary infection, dysuria, incontinence and retrograde ejaculation, can adversely affect a patient's willingness to undergo such a procedure.

A fairly recent alternative treatment method for BPH involves microwave thermal therapy, in which microwave energy is employed to elevate the temperature of tissue surrounding the prostatic urethra above about 45° C., thereby thermally damaging the tumorous tissue. At temperatures above about 45° C., healthy tissue is also thermally damaged. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation. The heat generated by the antenna is concentrated about the antenna in a generally cylindrically symmetrical pattern which encompasses and necroses tumorous tissue as well as healthy intraprostatic tissue to some degree. The necrosed intraprostatic tissue is subsequently reabsorbed by the body, thereby relieving an individual from the symptoms of BPH.

This microwave treatment method is derived from a treatment for prostatic cancer known as hyperthermia, in which microwave energy is supplied by a microwave antenna to the prostate to elevate the temperature of surrounding tissue to between about 43° C. to 45° C. Within this temperature range, healthy, well-vascularized tissue is unharmed because of the circulatory system's ability to effectively dissipate the heat by convection. Cancerous tissue, on the other hand, as reduced vascularity, which restricts its ability to adjust to the heat. Thus, heat concentrated in the region of the cancerous tissue is sufficient to necrose the cancerous tissue, yet insufficient to harm adjacent healthy tissue.

Microwave thermal therapy, because of its higher temperatures (above about 45° C.), provides the advantage of shortening a treatment session's duration as compared to that of hyperthermia with its lower temperatures (between about 43° C. and 45° C.). An undesirable consequence of microwave thermal therapy, however, is the adverse effect the higher temperatures have on healthy tissue adjacent the diseased area of the prostate, particularly the urethra, the ejaculatory duct and the rectum. The dilemma of selectively heating and necrosing only tumorous prostatic tissue by microwave thermal therapy has been successfully addressed in U.S. Pat. No. 5,413,588, entitled DEVICE FOR ASYMMETRICAL THERMAL THERAPY WITH HELICAL DIPOLE MICROWAVE ANTENNA, and U.S. Pat. No. 5,330,518, entitled METHOD FOR TREATING INTERSTITIAL TISSUE ASSOCIATED WITH MICROWAVE THERMAL THERAPY.

Antennas which have been used for hyperthermia have a variety of inadequacies which preclude their application to microwave thermal therapy. First, such antennas often generate heat in two forms: microwave energy and heat energy due to resistive losses of the antenna. The efficiency of these antennas has historically not been of much concern due to the relatively low amount of energy used to generate temperatures of between about 43° C. to 45° C. and the lack of any adverse effect these temperatures had on healthy tissue. Furthermore, it is known in the art that the shape and size of a radiation pattern generated by some microwave antennas are in part a function of how deeply the antenna is inserted into the tissue. Prior microwave dipole antennas used for hyperthermia have been unable to provide a predictable heating pattern within tissue due to the variable effects caused by the depth of insertion of the antennas into the tissue. Finally, the radiation length of these antennas has not been easily variable to accommodate the varying sizes of prostates requiring treatment. The antenna designs of the prior art relating to hyperthermia, therefore, have proven unsatisfactory for microwave thermal therapy and its attendant higher temperatures.

The objective of microwave thermal therapy is to reduce the length of a treatment session and to selectively heat and necrose only undesirous tissue, while sparing, to the greatest extent possible, adjacent healthy tissue. In order to avoid damage to tissues immediately adjacent the microwave antenna-containing applicator (i.e., the urethra, the ejaculatory duct and the rectum), it is essential that the resistive losses of the antenna be reduced or optimally eliminated.

The ability to eliminate resistive losses and utilize only microwave energy to heat a targeted tissue area permits a cooling system, such as that described in the above-referenced patents, to maintain safe temperatures adjacent to the applicator by absorbing and conveying away any excess heat conducted to the urethral tissues. In addition, an antenna capable of producing a predictable, yet selectively variable size heating pattern aids in achieving an effective treatment of undesirous tissue while minimizing harm to healthy tissue. An antenna with the above-described characteristics is described in U.S. Pat. No. 5,300,099, entitled GAMMA MATCHED HELICAL DIPOLE MICROWAVE ANTENNA, which is hereby incorporated by reference.

To further optimize the performance of the microwave energy delivery system, it is necessary to provide the capability to precisely detect forward power delivered to the microwave antenna and reflected power from the microwave antenna. There are several control functions that maybe enhanced by an improved dual-directional coupler for more precisely measuring forward and reflected power. For example, the microwave energy delivery system maybe designed to shut down upon detection of reflected power greater than a predetermined threshold, such as 10%, in order to safeguard the system against excessive heat buildup along the antenna and associated transmission line. Automatic frequency adjustment may be provided in the microwave generating source based on reflected power measurements, to optimize the impedance match and efficiency of the antenna within the frequency range available for therapy (e.g., 902–928 megahertz). The impedance of the microwave antenna may be dynamically adjustable according to reflected power measurements, as described in copending U.S. Application Ser. No. 08/621,634 filed Mar. 26,1996 for VOLTAGE CONTROLLED VARIABLE TUNING ANTENNA by E. Rudie. These and other schemes for controlling the microwave energy delivery system illustrate the utility and necessity of precise forward and reflected power detection capability.

SUMMARY OF THE INVENTION

The present invention is a microwave energy delivery system for microwave thermal therapy, an antenna and a transmission line connected to the antenna. A microwave generating source includes a generator connected to the transmission line and a dual directional coupler for detecting forward power delivered to the antenna and reverse power reflected from the antenna with an uncertainty of no more than 1%. According to one aspect of the invention, the power and/or frequency of the energy supplied by the generator is adjusted in response to the reverse power detected by the dual directional coupler.

In one embodiment, the dual directional coupler is a stripline apparatus including a first conductive trace for coupling microwave energy to the transmission line. A first terminating resistor is connected between the first conductive trace and ground. A first diode detection circuit is connected to the first conductive trace for detecting forward power coupled from the transmission line. A second conductive trace is provided for coupling to the transmission line, and a second terminating resistor is connected between the second conductive trace and ground. A second diode detection circuit is connected to the second conductive trace for detecting reverse power coupled from the transmission line.

BRIEF DESCRIPTION OF THE DRAWINGS

FIG. 8 is an exploded diagram illustrating the bottom portion of the dual directional coupler with channels formed therein for use in the microwave energy delivery system of the present invention.

DETAILED DESCRIPTION OF THE PREFERRED EMBODIMENTS

Figure 1:
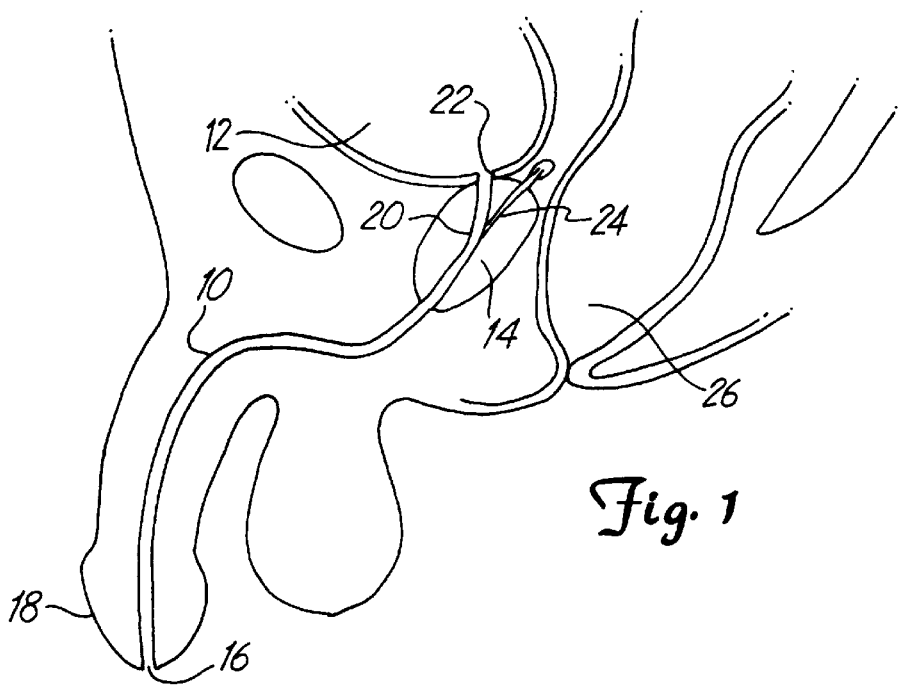
FIG. 1 is a vertical sectional view of a male pelvic region showing the urinary organs affected by benign prostatic hyperplasia.

FIG. 1 is a vertical section view of a male pelvic region showing the effect that benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) is made possible by a microwave antenna-containing catheter 28, insertable into urethra 10 as shown in FIG. 2.

Figure 2:
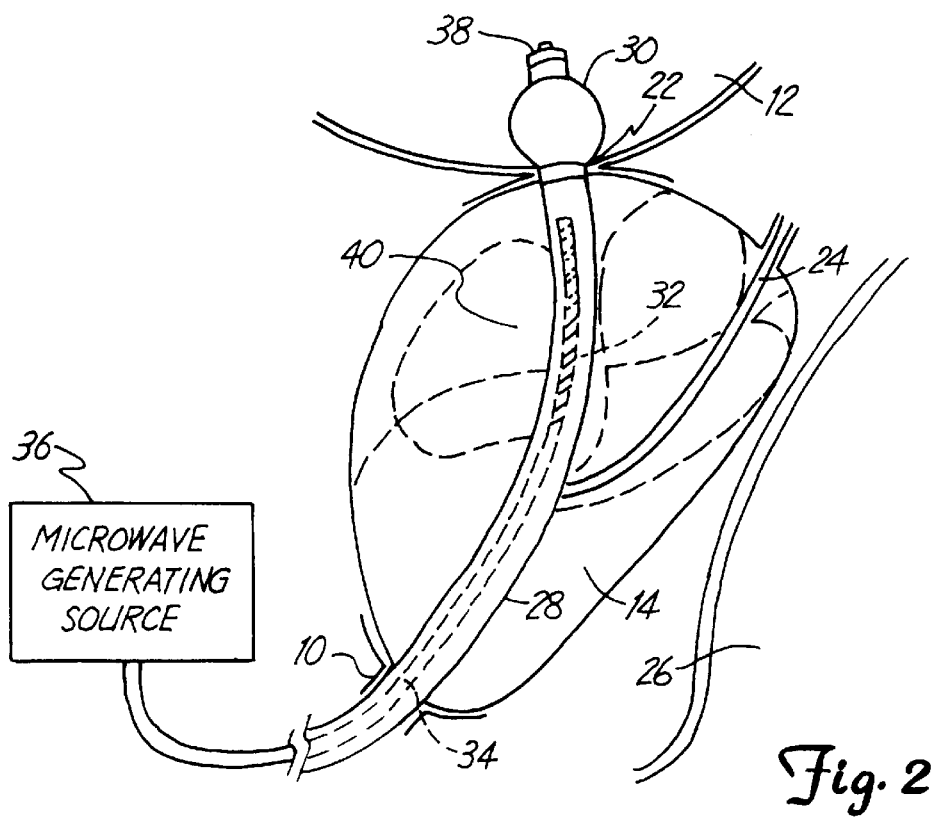
FIG. 2 is an enlarged view of the male pelvic region of FIG. 1 showing a urethral catheter positioned within the prostate region.

FIG. 2 shows an enlarged view of the male pelvic region of FIG. 1 with catheter 28 properly positioned within urethra 10. Catheter 28 includes retention balloon 30, end cap 38, and microwave antenna 32 connected to microwave generating source 36 by coaxial cable 34. Retention balloon 34 is inflated through an inflation port and lumen extending through catheter 28, and serves to retain catheter 28 in a fixed position within urethra 10 when balloon 34 is inflated within bladder 12 near bladder neck 22. The balloon inflation lumen is sealed at the end of catheter 28 by end cap 38.

In operation, microwave generating source 36 delivers a driving signal through coaxial cable 34 to energize microwave antenna 32. In a preferred embodiment, microwave generating source 36 produces a maximum of 100 watts of electrical power at about 915 MHz+/−13 MHz, which is within the U.S. FCC-ISM standards. When antenna 32 is energized by microwave generating source 36, antenna 32 emits electromagnetic energy which causes heating of tissue within transition region 40 of prostate 14 due to molecular excitation. Catheter 28 preferably includes a cooling system such as that described in U.S. Pat. No. 5,413,588, entitled DEVICE FOR ASYMMETRICAL THERMAL THERAPY WITH HELICAL DIPOLE MICROWAVE ANTENNA, which is hereby incorporated by reference. As a result, a relatively large portion of tissue enveloping the anterior portion of transition region 40 of prostate 14 is heated to a temperature above about 45° C., which effectively necroses the tumorous tissue of prostate 14 which encroaches upon urethra 10. The operation of catheter 28 preferably directs energy preferentially to maintain the temperature of tissue adjacent ejaculatory duct 24 and rectum 26 below about 45° C., and also preferably cools urethra 10 to avoid potential harmful effects to these tissues.

The use of an efficient microwave antenna is critical to the ability to focus thermal energy a distance from the antenna within a target tissue volume. An inefficient antenna produces a lesser intensity of microwave radiation within the target volume than desired. It also produces undesired heat close to the urethra along the antenna and associated transmission line, which will damage the urethra if not carried away by an increased coolant flow. This added burden on the cooling system limits its capacity to protect the urethra, thereby limiting the microwave power that can be radiated without elevating urethral temperatures above safety limits. With microwave power limited by cooling system capacity, the heat delivered to the desired target area of the prostate will not be sufficient for effective therapy. It is therefore critical to provide an efficient microwave antenna and also to provide a microwave energy delivery system that includes the capability to precisely detect forward and reflected power to and from the antenna, to monitor the efficiency of the antenna so that a condition where nearly all heat delivered during the treatment is delivered to the target tissue in the form of microwave energy, rather than reflected as conductive heat energy along the antenna and transmission line.

Figure 3:
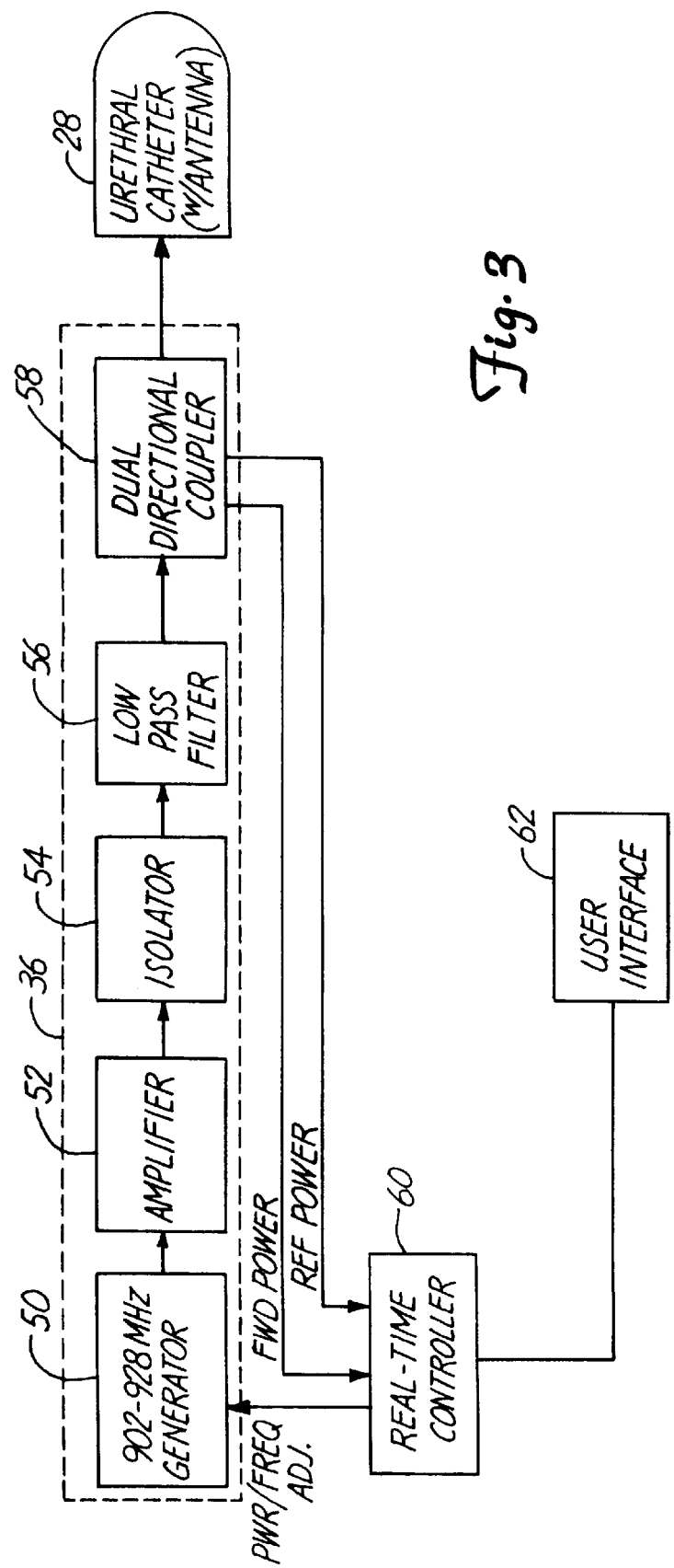
FIG. 3 is a block diagram of the microwave energy delivery system for use with a urethral catheter according to the present invention.
Figure 5:
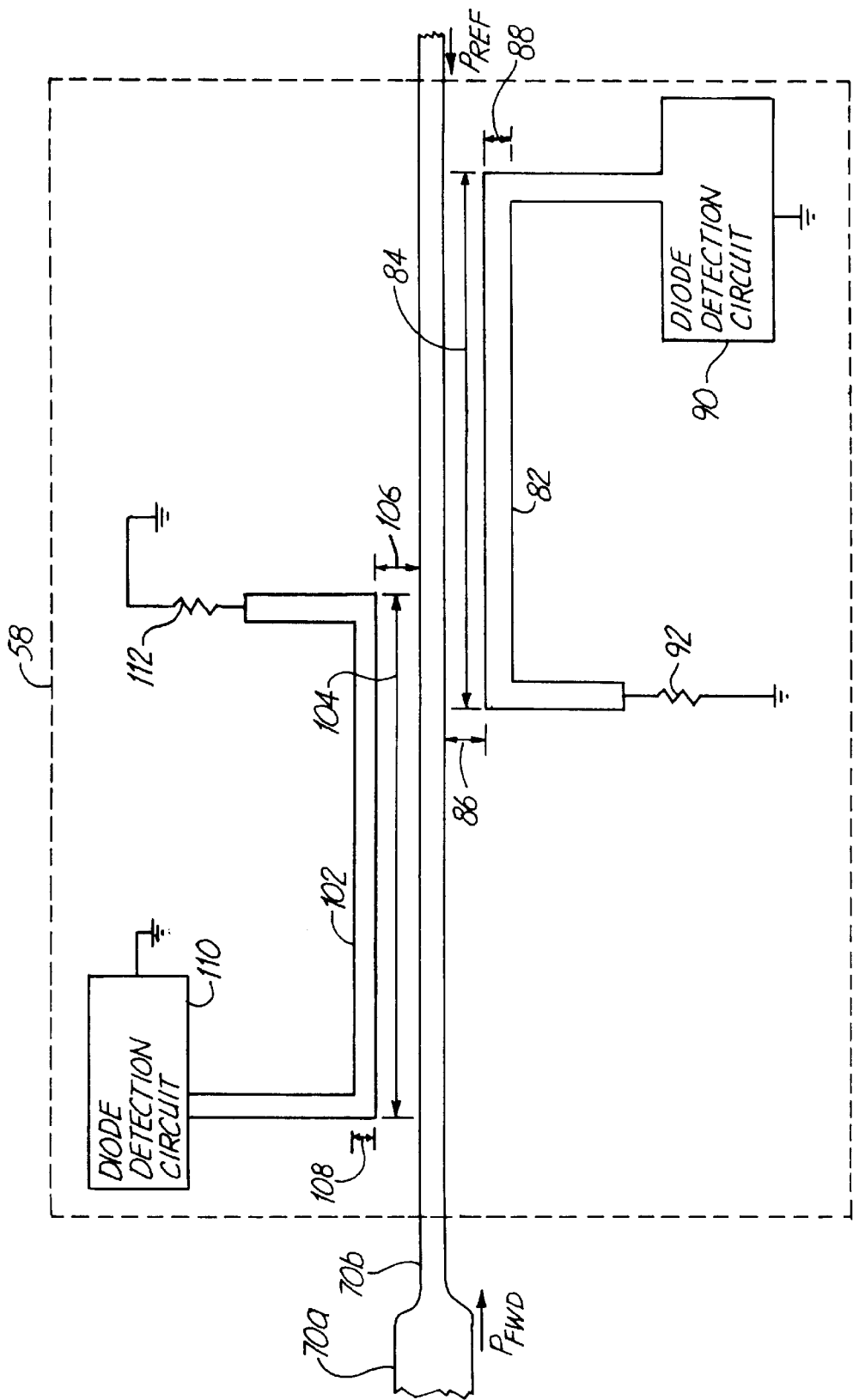
FIG. 5 is a schematic diagram of the dual directional coupler provided in the microwave energy delivery system to enable precise detection of forward and reflected microwave power.

FIG. 3 is a block diagram of a microwave energy delivery system for use with urethral catheter 28, according to the present invention. Microwave generating source 36 includes 902–928 MHz generator 50, amplifier 52, isolator 54, low pass filter 56 and dual directional coupler 58. Amplifier 52 steps up the signal from generator 50 to a level for delivering sufficient power to the microwave antenna for effective thermal therapy. Isolator 54 is provided to protect generator 50 and amplifier 52 from high level reflected power signals, thereby preserving the circuitry in cases where sudden coupling changes occur and cause large reflected power signals, for example. Low pass filter 56 attenuates high frequency harmonic signals, preferably by at least 30 dB, to ensure that those signals do not affect the performance of the microwave energy delivery system and antenna. Dual directional coupler 58 detects forward and reflected power, and is connected to real time controller 60 which analyzes the forward and reflected power measurements and is operable to control the power and/or frequency of generator 50 based on the forward and reflected power measurements. Generator 50, amplifier 52, isolator 54 and low pass filter 56 are implemented in a manner known in the art. Dual directional coupler 58 is preferably implemented as shown in FIG. 5, so that forward and reflected power may be precisely detected. User interface 62 is connected to real time controller 60, allowing a user to monitor the operation of the system and to input criteria and instructions for controlling the system via real time controller 60.

Figure 4:
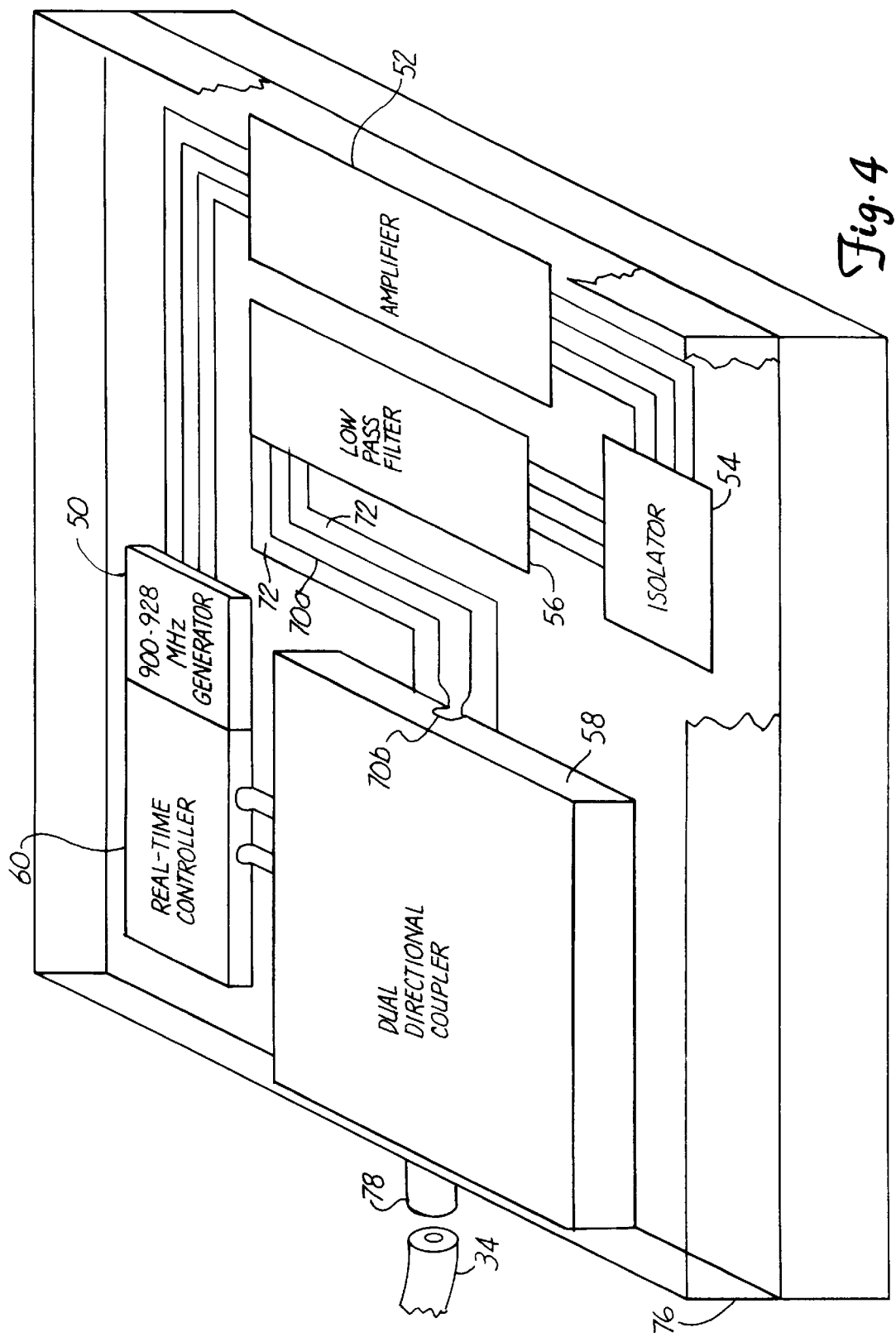
FIG. 4 is a perspective view of the microwave energy delivery system for use with a urethral catheter according to the present invention.

FIG. 4 is a perspective view of the microwave energy delivery system of the present invention. Amplifier 52, isolator 54 and low pass filter 56 are implemented using microstrip architecture in a manner known in the art. In a preferred embodiment, low pass filter 56 is implemented as a stepped impedance low pass filter, with transmission impedances selected to allow microstrip trace widths large enough to accommodate 100% reflected power, to account for the possibility of a fault condition. The microwave signal generated by generator 50 is passed through amplifier 52, isolator 54 and low pass filter 56 and to dual directional coupler 58 by a 50-ohm microstrip transmission line conductor 70a. The width of transmission line conductor 70a and surrounding dielectrics 72 and 74 are designed so that microstrip transmission line 70a performs as a 50-ohm characteristic impedance coaxial cable, according to techniques known in the art. The transmission line is then narrowed into transmission line 70b as it passes through dual directional coupler 58, which is implemented in a stripline architecture, having a conductor formed on a dielectric layer with another dielectric layer above, between two parallel ground planes, as is known in the art. Transmission line 70b is also designed according to techniques known in the art to perform as a 50-ohm characteristic impedance coaxial cable, and is narrower than microstrip transmission line 70a to account for the differences in performance characteristics between microstrip and stripline architectures. The microwave energy delivery system is housed in chassis 76, with a microwave flat-to-round connector 78 providing an interface through chassis 76 between dual directional coupler 58 and coaxial cable 34.

FIG. 5 is a schematic diagram of dual directional coupler 58 for enabling precise detection of forward and reflected microwave power. Conductive trace 82 runs parallel to transmission line conductor 70b for a length 84 equal to a quarter wavelength at the median microwave operating frequency (e.g. 915 MHz). The microwave signal on transmission line conductor 70b is coupled to conductive trace 82 across capacitive gap 86. The forward power signal on transmission line conductor 70b is coupled onto conductive trace 82 with a predetermined amount of attenuation, which is controlled by length 84 of conductive trace 82, gap 86 between transmission line conductor 70b and conductive trace 82, and width 88 of conductive trace 82, as is known in the art of high frequency coupler design. The coupling structure operates to attenuate the coupled signal down to an appropriate level for measurement, and effectively blocks any reflected power signal from being coupled onto conductive trace 82, so that forward and reflected power measurements are substantially unaffected by each other. Diode detection circuit 90 is connected to conductive trace 82, and operates to detect the forward power signal. A terminating resistor traditionally is selected to present an impedance matched to the characteristic impedance of transmission line 70b; however, terminating resistor 92 of the present invention is intentionally chosen to present an impedance mismatch to compensate for degradation effects associated with manufacturing variations in the coupling circuit. This design results in optimal directivity (a measure of separation between forward power measurements and reverse power measurements) and therefore precision in measuring forward power.

Similar to that described above, conductive trace 102 runs parallel to transmission line conductor 70b for a length 104 equal to a quarter wavelength at the median microwave operating frequency (e.g. 915 MHz). The microwave signal on transmission line conductor 70b is coupled to conductive trace 102 across capacitive gap 106. The reflected power signal on transmission line conductor 70b is coupled onto conductive trace 102 with a predetermined amount of attenuation, which is controlled by length 104 of conductive trace 102, gap 106 between transmission line conductor 70b and conductive trace 102, and width 108 of conductive trace 102, as is known in the art of high frequency coupler design. The coupling structure operates to attenuate the coupled signal down to an appropriate level for measurement, and effectively blocks any forward power signal from being coupled onto conductive trace 102, so that reflected and forward power measurements are substantially unaffected by each other. Diode detection circuit 110 is connected to conductive trace 102, and operates to detect the reflected power signal. Once again, terminating resistor 112 of the present invention is intentionally chosen to present an impedance mismatch to compensate for degradation effects associated with manufacturing variations in the coupling circuit. This design results in optimal directivity and therefore precision in measuring reflected power.

Figure 6:
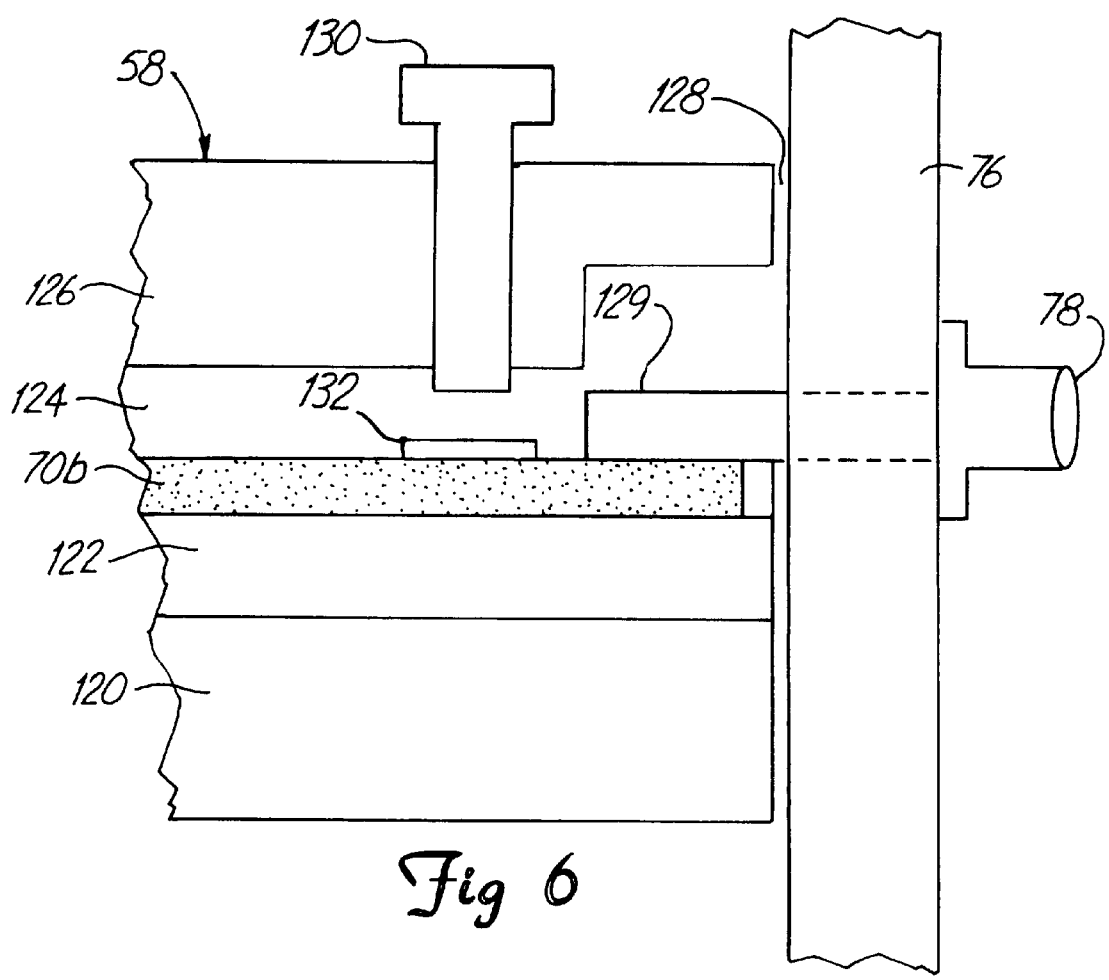
FIG. 6 is a diagram illustrating a tuning screw for use with the microwave energy delivery system of the present invention.

FIG. 6 is a diagram illustrating the interface between dual directional coupler 58 and flat-to-round connector 78, implementing tuning screw 130 according to the present invention. Dual directional coupler 58 includes transmission line conductor 70b formed on dielectric layer 122 with dielectric layer 124 above, between conductive ground planes 120 and 126. In a preferred embodiment, the layers of dual directional coupler 58 are torqued together so that transmission line conductor 70b is effectively embossed into dielectric layers 122 and 124, to prevent air gaps between dielectric layers 122 and 124 due to the thickness of conducto70b. Dual directional coupler 58 extends adjacent to the wall of chassis 76, with air gap 128 between dual directional coupler 58 and chassis wall 76. Connector 78 includes conductive element 129 extending through chassis wall 76 to contact transmission line conductor 70b, to couple the microwave signal from transmission line conductor 70b to coaxial cable 34 (FIG. 4) for delivery to a microwave antenna in a treatment catheter.

Air gap 128 between dual directional coupler 58 and chassis wall 76 introduces a parasitic inductance and capacitance into the system, while the flat-to-circular transition at connector 78 introduces a parasitic inductance. While the ranges of these parasitic effects may be controlled, it is nearly impossible to control the manufacturing process tightly enough to consistently and precisely cancel the parasitics, which presents the potential for an impedance mismatch that would degrade the efficiency of microwave power delivery to the prostate. Additionally, it is possible for coaxial cable 34 (FIG. 4) to present a characteristic impedance that is not exactly 50 ohms, due to inexact manufacturing, which needs to be accounted for by the microwave energy delivery system if performance is to be optimized. Therefore, the manufacturing process is controlled to ensure that the parasitic effects due to air gap 128 and the flat-to-circular transition of connector 78 result in a net parasitic inductance, and tuning screw 130 is provided to extend through ground conductor 126 into dielectric layer 124 to present an adjustable capacitance in the system to cancel the net parasitic inductance. The capacitance is adjustable by simply turning screw 130 to change the depth that screw 130 extends into dielectric layer 124. The capacitance is directly related to the distance between transmission line conductor 70b and the tip of screw 130. Mica insulator 132 is preferably provided in dielectric layer 124 opposing the tip of screw 130 to protect against shorting between tuning screw 130 and transmission line conductor 70b; tuning screw 130 can be turned until it contacts insulator 132 adjacent transmission line conductor 70b. Insulator 132 may alternatively be composed of an insulating material known in the art other than mica. In one embodiment, calibration of the system is initially performed while connecter 78 is connected to a standardized 50-ohm load termination, with tuning screw 130 being adjusted until 0% reflected power is achieved, and is then performed again with a patient cable in place to account for variations in the patient cable from the nominal 50-ohm characteristic impedance. Thus, tuning screw 130 may be adjusted until the efficiency of the microwave antenna delivery system is maximized, providing the capability to achieve optimum impedance matching performance despite minor characteristic impedance variations in coaxial cable 34 and other components of the thermal therapy system.

Figure 7:
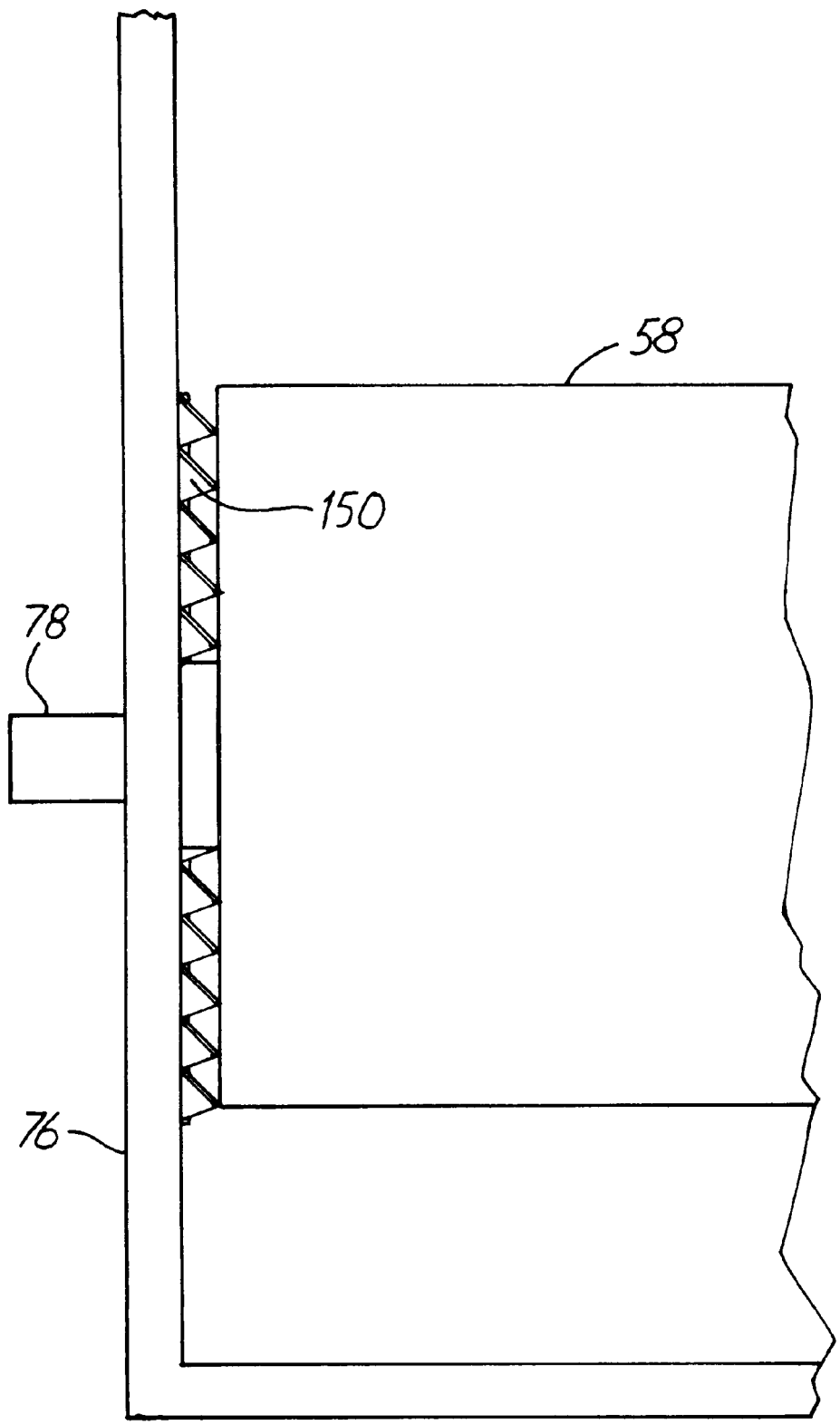
FIG. 7 is a top view illustrating a twisted wire gasket for providing a low inductance ground in the microwave energy delivery system of the present invention.

FIG. 7 is a top view illustrating twisted wire gasket 150 positioned between dual-directional coupler 58 and chassis wall 76 to provide a low inductance ground in the microwave energy delivery system of the present invention. Twisted wire gasket 150 may, for example, be a dual twist contact strip, part number 99-220-NT commercially available from Omega Shielding Products. Twisted wire gasket 150 contacts the metal surfaces (conductors 120 and 126, FIG. 6) of dual directional coupler 58 and also the metal surface of chassis wall 76, effectively "gouging" into those metal surfaces and thereby achieving superior contact between them. This is desirable to reduce the noise associated with the ground of the microwave energy delivery system due to inductance in ground connections. Chassis wall 76 and outer conductors 120 and 126 (FIG. 6) of dual directional coupler 58 are grounded, so that the low inductance connection between them provided by twisted wire gasket 150 is beneficial to reduce the noise level associated with the ground of the system, thereby improving the sensitivity and overall performance of the system.

FIG. 8 is an exploded diagram illustrating the bottom portion of dual directional coupler 58 with channels 160, 162, 164 and 166 formed therein for use in the microwave energy delivery system of the present invention. Channels 160 and 162 are formed with sufficient depth to house diode detection circuits 90 and 110 (FIG. 5), which may be realized on a conventional PC board, for example, or by other well-known circuit construction technologies. Corresponding channels are formed in the top portion of dual directional coupler 58 opposite channels 160 and 162, thereby forming recessed cavities within the body of dual directional coupler 58 that effectively shield diode detection circuits 90 and 110 (FIG. 5) from external noise, improving their sensitivity and overall performance.

Channels 164 and 166 are formed with a width and depth to enable wire mesh pieces 170 to be inserted therein. Wire mesh pieces 170 may, for example, be hollow core round ultraflex electronic beryllium copper knitted wire shielding pieces, part number 8101-0104-40 (0.156 inch diameter) commercially available from Instrument Specialties. Wire mesh pieces 170 are preferably inserted into channels 164 and 166 so that there is a slight crest of mesh material above the top of the channels. Wire mesh pieces 170 inserted in channels 164 and 166 improve the electrical connection between the top and bottom portions of dual directional coupler 58, specifically between ground plane conductors 120 and 126 (FIG. 6), improving the grounding distribution properties and thereby improving the sensitivity and overall performance of dual directional coupler 58.

The present invention therefore provides a microwave energy delivery system having the capability to precisely detect both forward power delivered to a microwave antenna and reverse power reflected from the microwave antenna. This is achieved by a dual directional coupler, which is preferably connected to a real time controller to analyze the forward and reflected power measurements. The dual directional coupler includes a first quarter wavelength coupling circuit to detect forward power signals on the main transmission line and second quarter wavelength coupling circuit to detect reflected power signals from the transmission line. Terminating resistors for each coupling circuit are selected to have impedances that are mismatched from the characteristic impedance of the transmission line to optimize the directivity of the dual directional coupler. The dual directional coupler is preferably tunable to optimize the impedance match and thereby performance of the system. Additionally, a twisted wire gasket and wire mesh pieces are preferably utilized in association with the dual directional coupler to improve the ground distribution of the system. The above-described features thereby provide a microwave energy delivery system with a high performance dual directional coupler, capable of measuring forward and reflected power with an uncertainty of no more than about 1%, which is a substantial improvement over previous devices that typically experienced uncertainty on the order of 8%.

For example, a dual-directional coupler constructed as described above was implemented in a microwave energy delivery system and tested at a center frequency of 915 MHz, yielding the results shown in Table 1.

TABLE 1

| Terminating Resistor Values | Through-Line Power | Coupling | Isolation |
|---|---|---|---|
| 49.9 ohms | −0.08 dB | −26.5 dB | −41.4 dB |
| 47.5 ohms | −0.08 dB | −26.1 dB | −45.6 dB |
| 43.1 ohms | −0.08 dB | −25.8 dB | −40.0 dB |

The Terminating Resistor Values represent the values of terminating resistors 92 and 112 (FIG. 5). The Through-Line Power value represents the reduction in power delivered on transmission line conductor 70b due to coupling by dual-directional coupler 58. The Coupling value represents the ratio of the coupled power signal on traces 82 and 102 to the delivered power signal on transmission line conductor 70b. The Isolation value represents the ratio of a voltage signal representing the undesired power signal to a voltage signal representing the desired power signal; that is, the ratio of a reflected power voltage signal to a forward power voltage signal in the forward power detection circuit, and the ration of a forward power voltage signal to a reflected power voltage signal in the reflected power detection circuit. Higher Isolation values mean that forward (or reflected) power measurements can be obtained with less uncertainty caused by effects of reflected (or forward) power signals. As can be seen from Table 1, Terminating Resistor Values of 47.5 ohms yielded the greatest Isolation in the dual-directional coupler tested. An Isolation value of −40 dB represents an uncertainty of 1%, meaning that a reflected power signal (in the forward power detection circuit) has a magnitude that is attenuated to 1% of its actual (coupled) magnitude while the forward power signal has its 100% full (coupled) magnitude, and vice versa for the forward power signal in the reflected power detection circuit. As a result, the microwave energy delivery system of the present invention is able to utilize precise forward and reflected power measurements to perform a variety of control functions, thereby optimizing the performance of the system in a thermal therapy treatment session.

Although the present invention has been described with reference to preferred embodiments, workers skilled in the art will recognize that changes may be made in form and detail without departing from the spirit and scope of the invention.

What is claimed is:

1. A microwave energy delivery system for microwave thermal therapy, comprising:

an antenna;

a transmission line connected to the antenna; and a microwave generating source including a generator connected to the transmission line and a dual directional coupler for measuring forward power delivered to the antenna and reverse power reflected from the antenna with an uncertainty of no more than 1%.

2. The microwave energy delivery system of claim 1, wherein the dual directional coupler is a stripline apparatus comprising:

a first conductive trace for coupling to the transmission line;

a first terminating resistor connected between the first conductive trace and ground;

a first diode detection circuit connected to the first conductive trace for detecting forward power coupled from the transmission line;

a second conductive trace for coupling to the transmission line;

a second terminating resistor connected between the second conductive trace and ground; and a second diode detection circuit connected to the second conductive trace for detecting reverse power coupled from the transmission line.

3. The microwave energy delivery system of claim 2, wherein the first and second terminating resistors are selected to introduce an impedance mismatch between the first and second terminating resistors and the transmission line.

4. The microwave energy delivery system of claim 2, wherein the first and second conductive traces each have a length equal to a quarter wavelength at an operating frequency of the generator.

5. The microwave energy delivery system of claim 1, wherein the dual directional coupler further includes a tuning screw for introducing a variable capacitance to precisely match a range of impedances associated with the transmission line.

6. The microwave energy delivery system of claim 1, wherein the dual directional coupler is mounted on a chassis, and further comprising a twisted wire gasket between the dual directional coupler and a wall of the chassis for distributing a ground of the system.

7. The microwave energy delivery system of claim 1, wherein the dual directional coupler further comprises first and second ground plane conductors and a plurality of channels between the first and second ground plane conductors having wire mesh pieces therein to distribute a ground of the system.

8. The microwave energy delivery system of claim 1, further comprising an isolator connected between the generator and the dual directional coupler to block reflected power from reaching the generator.

9. The microwave energy delivery system of claim 8, wherein the isolator is implemented as a microstrip structure.

10. The microwave energy delivery system of claim 1, further comprising a low pass filter connected between the generator and the dual directional coupler to attenuate high frequency harmonics signals from the generator.

11. The microwave energy delivery system of claim 10, wherein the low pass filter is implemented as a microstrip structure.

12. The microwave energy delivery system of claim 1, wherein the microwave generating source generates energy having a frequency between 902 and 928 MHz.

13. A microwave energy delivery system for microwave thermal therapy, comprising:

an antenna;

a transmission line connected to the antenna; and a microwave generating source comprising:

a generator connected to the transmission line, the generator supplying energy o f selectively controlled power and with a frequency that is selectively controlled in a range of 902 and 928 MHz;

a dual directional coupler for detecting forward power delivered to the antenna and reverse power reflected from the antenna with an uncertainty of no more than about 1%; and a controller for adjusting the power and/or frequency of the energy supplied by the generator in response to the reverse power detected by the dual directional coupler.

14. The microwave energy delivery system of claim 13, wherein the dual directional coupler is a stripline apparatus comprising:

a first conductive trace for coupling to the transmission line;

a first terminating resistor connected between the first conductive trace and ground;

a first diode detection circuit connected to the first conductive trace for detecting forward power coupled from the transmission line;

a second conductive trace for coupling to the transmission line;

a second terminating resistor connected between the second conductive trace and ground; and a second diode detection circuit connected to the second conductive trace for detecting reverse power coupled from the transmission line.

15. The microwave energy delivery system of claim 14, wherein the first and second terminating resistors are selected to introduce an impedance mismatch between the first and second terminating resistors and the transmission line.

16. The microwave energy delivery system of claim 14, wherein the first and second conductive traces each have a length equal to a quarter wavelength at an operating frequency of the generator.

17. The microwave energy delivery system of claim 13, wherein the dual directional coupler further includes a tuning screw for introducing a variable capacitance to precisely match a range of impedances associated with the transmission line.

18. The microwave energy delivery system of claim 13, wherein the dual directional coupler is mounted on a chassis, and further comprising a twisted wire gasket between the dual directional coupler and a wall of the chassis for distributing a ground of the system.

19. The microwave energy delivery system of claim 13, wherein the dual directional coupler further comprises first and second ground plane conductors and a plurality of channels between the first and second ground plane conductors having wire mesh pieces therein to distribute a ground of the system.

* * * * *